(12) United States Patent
Callne

(10) Patent No.: US 7,083,410 B2
(45) Date of Patent: Aug. 1, 2006

(54) DENTAL ARTICULATOR

(75) Inventor: Lars Callne, Fallbrook, CA (US)

(73) Assignee: Vident, Brea, CA (US)

( * ) Notice: Subject to any disclaimer, the term of this patent is extended or adjusted under 35 U.S.C. 154(b) by 0 days.

(21) Appl. No.: 10/869,008

(22) Filed: Jun. 16, 2004

(65) Prior Publication Data

US 2005/0282105 A1  Dec. 22, 2005

(51) Int. Cl.
*A61C 11/00* (2006.01)
(52) U.S. Cl. .......................................... 433/58; 433/60
(58) Field of Classification Search ............. 433/57–67
See application file for complete search history.

(56) References Cited

U.S. PATENT DOCUMENTS

| | | | |
|---|---|---|---|
| 2,688,800 A | 9/1954 | Gerber | |
| 3,466,750 A | 9/1969 | Timberlake et al. | |
| 4,045,873 A * | 9/1977 | Burnett | 433/58 |
| 4,175,325 A | 11/1979 | Beckwith | |
| 4,382,787 A | 5/1983 | Huffman | |
| 4,556,387 A * | 12/1985 | Lee | 433/58 |
| 4,797,097 A | 1/1989 | Cohn | |
| 4,865,544 A | 9/1989 | Scruggs | |
| 5,026,282 A * | 6/1991 | Koike | 433/62 |
| 5,320,528 A * | 6/1994 | Alpern et al. | 433/58 |
| 5,366,373 A | 11/1994 | Mumolo et al. | |
| 5,425,636 A | 6/1995 | Ghim | |
| 5,531,595 A * | 7/1996 | Koutavas | 433/65 |
| 5,645,425 A | 7/1997 | Callne | |
| 5,769,634 A | 6/1998 | Choi | |
| 6,382,969 B1 | 5/2002 | Elnajjar | |

* cited by examiner

*Primary Examiner*—John J Wilson
(74) *Attorney, Agent, or Firm*—Calif Tervo; Palomar Patent

(57) ABSTRACT

A dental articulator for connecting upper and lower dental models made from dental impressions of teeth and for moving the mandible in opening and closing, protrusive and lateral motions generally comprises upper and lower arms each having a front end for attachment respectively to upper or lower model. The upper arm includes a pair of condylar slots for receiving journals of the lower arm such that the lower arm may perform the opening and closing motion, the protrusive movement, and lateral movement of the mandible. A cantilever spring attached to the upper arm biases the journals toward the centric occlusion position. Slot stops limit protrusive movement and axle stops limit lateral movement.

14 Claims, 2 Drawing Sheets

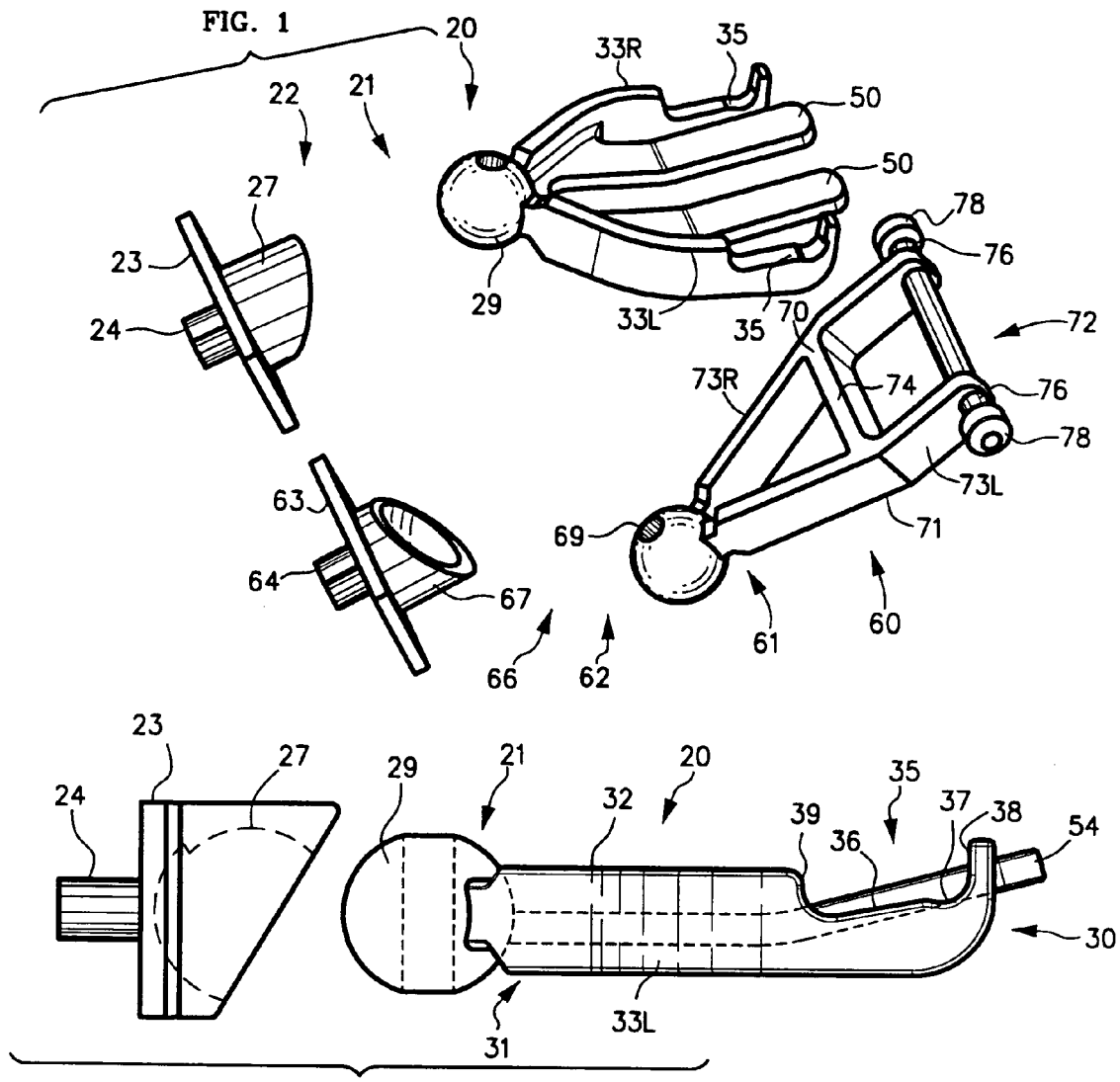
FIG. 1
FIG. 2
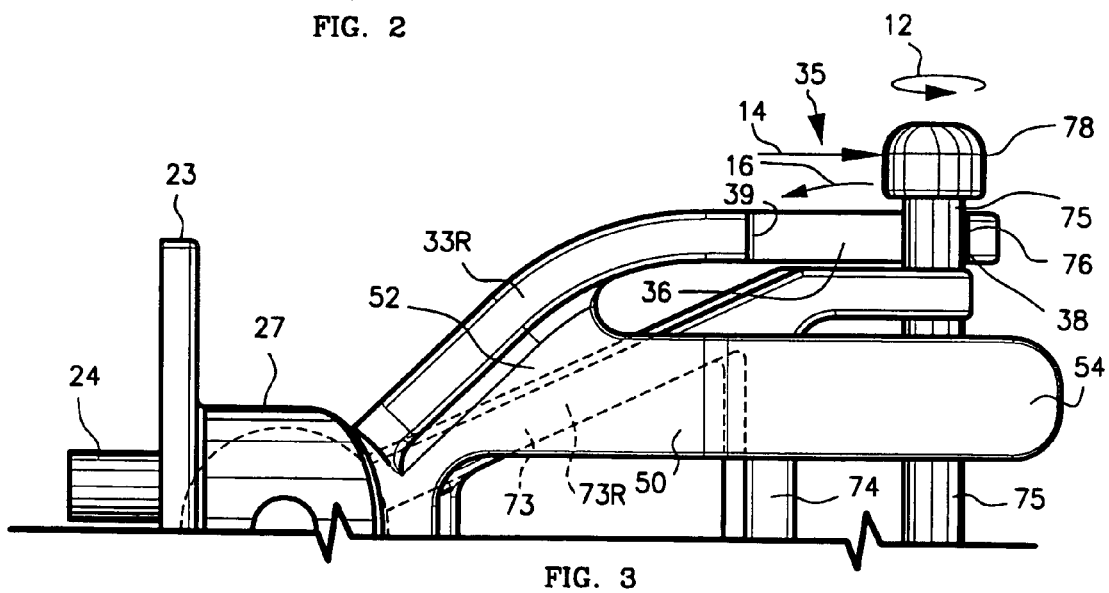
FIG. 3

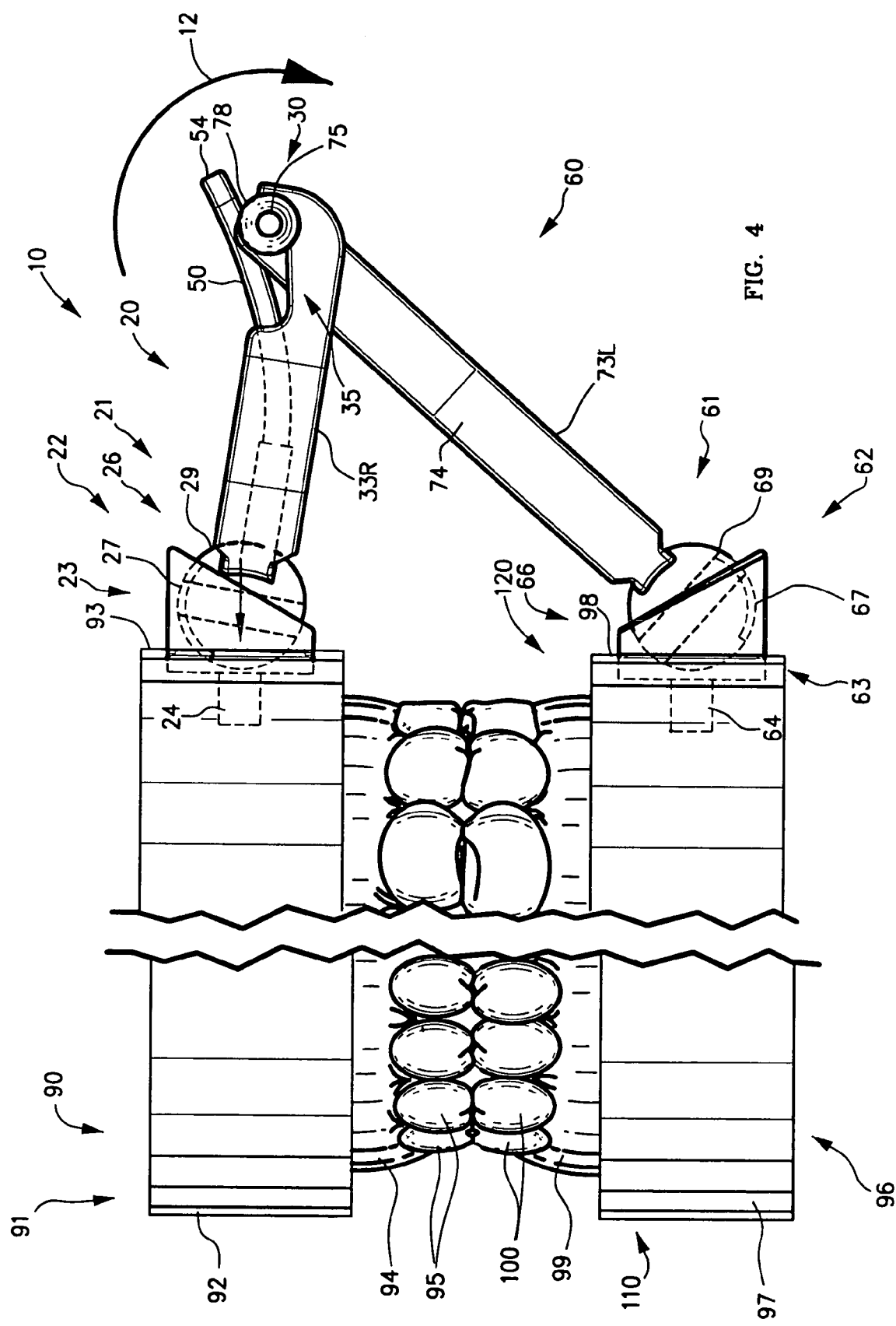

DENTAL ARTICULATOR

FIELD OF THE INVENTION

This invention relates in general to dental articulators, and more specifically involves a disposable dental articulator that emulates the movements of the mandible.

BACKGROUND OF THE INVENTION

Articulators or correlators for use with casts of a dental model to develop dental prostheses or denture elements have been used for a number of years. These articulators range from a very simple device affording only fixed pivotal movement between a pair of casts to highly sophisticated and mechanically complex devices which are capable of simulating the full range of occlusal and masticatory registration unique to any patient. The relatively simple devices are generally inadequate to provide sufficiently accurately registered prosthetic restoration and, thus, may require the patient to make many visits with a dentist to obtain adjustments thereof. On the other hand, the very complex devices are time consuming to operate and require extensive training to use properly. In either situation, the costs to the patient are substantial.

Many conventional articulators include anchors in the dental casts that fix the angle of attachment of the articulator. If the casts are not made perfectly level to one another, then the articulator does not move the casts properly.

Moreover, many of the prior art articulators do not permit disengagement of the casts from registration with one another without extensive realignment upon reengagement. Thus, a technician may have to perform work while the casts are mounted on the articulator. It is difficult to work with speed and accuracy when the articulator is mounted to the casts.

Therefore, there has been a need for a simple disposable dental articulator for mounting and adjustably holding casts of a dental model that simulates all of the mandible motions.

It is further desirable that the articulator easily attaches to dental casts at any angle to make up for casts not being level.

It is further desirable that the articulator permits rapid disassembly and reassembly without the need of realignment to effect proper registration between the casts.

SUMMARY OF THE INVENTION

The invention is a dental articulator for connecting upper and lower dental models and for moving the mandible in opening and closing, protrusive, and lateral motions. The articulator generally comprises upper and lower arms, each having a front end for attachment to its respective upper or lower dental model. The upper arm includes a pair of laterally spaced, longitudinally oriented condylar slots, each for receiving a journal.

The lower arm includes a pair of laterally spaced, laterally oriented journals adapted for disposition in the slots such that the lower arm may pivot about the journals relative to the upper arm to perform the opening and closing motion of the mandible, such that the journals may jointly longitudinally slide in the slot such that the lower arm moves longitudinally relative to the upper arm to perform the protrusive movement of the mandible, and such that the journals may independently longitudinally slide in the slot such that the front end of the lower arm moves laterally relative to the upper arm to perform the lateral movement of the mandible.

A cantilever spring attached to the upper arm biases the journals toward the centric occlusion position. Slot stops limit protrusive movement and axle stops limit lateral movement.

Other features and many attendant advantages of the invention will become more apparent upon a reading of the following detailed description together with the drawings wherein like reference numerals refer to like parts throughout.

BRIEF DESCRIPTION OF THE DRAWINGS

FIG. 1 is a top front left exploded perspective view of a preferred embodiment of the dental articulator of the invention.

FIG. 2 is an enlarged exploded side elevation view of the upper arm of FIG. 1.

FIG. 3 is a top plan view of the right half of the articulator of FIG. 1 assembled; the left half being a mirror image.

FIG. 4 is a left side elevation view of the articulator of FIG. 1 attached to a dental model.

DETAILED DESCRIPTION OF THE INVENTION

Looking now at the drawings, FIG. 1 is a top front left exploded perspective view of a preferred embodiment of the dental articulator 10 of the invention. Articulator 10 generally includes an upper arm 20 and a lower arm 60. FIG. 2 is an enlarged exploded side elevation view of upper arm 20. FIG. 3 is a top plan view of the right half of articulator 10 assembled; the left half being a mirror image. FIG. 4 is a left side elevation view of articulator 10 attached to a dental model 90.

As best seen in FIG. 4, dental model 90 includes an upper dental model 91 and a lower dental model 96. Upper dental model 91 includes a base 92 having a rear face 93 and a maxilla cast 94 of upper teeth 95. Lower dental model 96 includes a base 97 having a rear face 98 and a mandible cast 99 of lower teeth 100.

Dental articulator 10 connects upper dental model 91 with lower dental model 96. Upper arm 20 includes a front end 21 including upper arm attaching means 22 for attaching upper arm 20 to upper dental model 91. Upper arm attaching means 22 includes an upper anchor 23 including a forward tab 24 attached to upper dental model 91 by any suitable method, many of which are well-known in the art. Anchor 23 and front end 21 of upper arm 20 include cooperating attachment means 26, such as socket 27 on upper anchor 23 and snap-in ball 29 on front end 21, for attaching upper arm 20 to upper model 91, preferably at any angle so as to allow the proper spatial relationship between upper cast 94 and lower cast 99 to be adjusted. Lower arm 60 includes a front end 61 including lower arm attaching means 62 for attaching lower arm 60 to lower dental model 96. Lower arm attaching means 62 may be similar to the upper arm attaching means 22 and include a lower anchor 63 including a forward tab 64 attached to lower dental model 96 by any suitable method, many of which are well-known in the art. Lower anchor 63 and front end 61 of lower arm 60 include cooperating attachment means 66, such as socket 67 on lower anchor 63 and snap-in ball 69 on front end 61, for attaching lower arm 60 to lower model 96, preferably at any angle so as to allow the proper spatial relationship between upper cast 94 and lower cast 99 to be adjusted. When all elements are in proper alignment, balls 29, 69 are fixed, such as by gluing, in sockets 27, 67. Ball sockets are particularly desirable for use as cooperative connectors because they may be adjusted to any angle. However, other methods of attachment are well-known in the art and may be used. The direction between front 110 and rear 120 of dental model 90 defines the longitudinal direction.

Now including the other figures, upper arm 20 has a front end 21, a rear end 30, a bottom 31, and a top 32. Upper arm 20 includes two curved arms 33, left arm 33L and right arm 33R, in a generally U-shaped configuration from the front in top view. Near the top rear end of arms 33 are a pair of laterally spaced, upward facing, longitudinally oriented, journal receiving surfaces, such as condylar slots 35 having a bottom surface 36 for receiving a journal.

Lower arm 60 includes a front end 61, a top 70, a bottom 71 and a rear end 72. Lower arm 60 includes two arms 73, left arm 73L and right arm 73R, in a generally V-shaped configuration from the front in top view. A stabilizing bar 74 joins arms 73L, 73R near midsection to add stability and strength. Attached near the rear end of arms 73 is a lateral axel or shaft 75 including a pair of laterally spaced and laterally oriented journals 76 adapted for disposition on said slot bottoms 36 such that lower arm 60 may pivot about journals 76 relative to upper arm 20 to perform the opening and closing motion of upper and lower dental models 91, 96; journals 76 may jointly longitudinally slide on slot bottom 36 such that lower arm 60 moves longitudinally relative to upper arm 20 to perform the protrusive movement of dental model 90 and journals 76 may independently longitudinally slide on slot bottom 36 such that front end 61 of lower arm 60 moves laterally relative to front end 21 of upper arm 20 to perform the lateral movement of dental model 90. These three movements, hinge 12, protrusive 14 and lateral 16, are best seen in FIGS. 3 and 4.

Slots 35 includes a rear stop 38 and a front stop 39 that function as longitudinal restraining means for restraining longitudinal travel of journals 76. Slot bottom 36 includes a small recess 37 adjacent rear stop 38.

Biasing means, such as cantilevered springs 50, bias journals 76 on journal receiving surfaces 36 toward a predetermined position, such as toward the centric occlusion position as shown in FIG. 4 wherein journals 76 are at the rear of slot 36 and in the recess 37 wherein dental models 91, 96 are in standard engaged position. Springs 50 have a front end 52 connected to upper arm 20 near front end 21 and a rear end 54. Springs 50 have a neutral position as shown in FIG. 2. Preferably, rear end 54 is rearward of upper arm 20 so that, upon joining upper and lower arms 20, 60, journals 76 push springs 50 upward and away from slot 35 so that journals 76 can enter slot 35. Recess 37 requires a small additional force to move dental models 91, 96 from the centric occlusion position.

Although front stops 39 and rear stops 38 serve as longitudinal restraining means for restraining longitudinal travel of journals 76, other longitudinal restraining means are contemplated. For example, springs 50 may stop forward travel or springs 50 may have downward protrusions that function as front and rear stops. With spring 50 so designed, slot 35 is not necessary and the journal receiving surface may be top 32 of arms 20.

Enlargements such as lateral stops 78 on axel 75 provide lateral restraining means for restraining relative individual travel of journals 76 on slot bottom 36. As best seen in FIG. 3, each journal 76 is wider than the width of its slot 35 such that when one journal 76 moves relative to the other journal 76 to produce relative lateral movement of dental models 91, 96, journals 76 remain on slot bottom 36. Lateral stops 78 are spaced adjacent journals 76 on axel 75. At maximum allowable relative lateral movement, lateral stop 78 will encounter upper arm 20 and stop further rotation.

Preferably, the length of lower arm from ball 69 to shaft 75 is longer than the length of upper arm 20 from ball 29 to the rear end of slot 36, such as to detent 37, such that the rotational axis of axle 75 in the centric occlusion position is above the plane of the teeth opening as shown in FIG. 4. Preferably, bottom 36 of slot 35 is horizontal or within fifteen degrees of horizontal to more closely simulate dental movement.

From the foregoing description, it is seen that the present invention provides an extremely efficient and reliable dental articulator that is easy to use and is able to simulate all of the different motions of the mandible, that is opening and closing, protrusive and lateral motions. The articulator can be attached to the dental model with model and articulator in the centric occlusion position and the arms are easily detached from one another such that work can be performed on either upper or lower model and then easily reengaged. Yet, the articulator is so simple and inexpensive as to be disposable.

Although a particular embodiment of the invention has been illustrated and described, various changes may be made in the form, composition, construction, and arrangement of the parts herein without sacrificing any of its advantages. Therefore, it is to be understood that all matter herein is to be interpreted as illustrative and not in any limiting sense, and it is intended to cover in the appended claims such modifications as come within the true spirit and scope of the invention.

I claim:
1. A dental articulator for connecting upper and lower dental models, each having a front and a rear, the front to rear direction defining the longitudinal direction; said dental articulator including:
an upper arm including:
a front end including:
upper attaching means for attaching said front end of said upper arm to the upper dental model;
a rear end;
a bottom;
a top; and
a pair of laterally spaced, longitudinally oriented, journal receiving surfaces;
a lower arm including:
a front end including:
lower attaching means for attaching said front end of said lower arm to the lower dental model;
a top;
a bottom;
a rear end;
a pair of laterally spaced, laterally oriented journals adapted for disposition on said journal receiving surfaces such that: said lower arm may pivot about said journals relative to said upper arm to perform the opening and closing motion of the dental models; said journals may jointly longitudinally slide on said journal receiving surfaces such that said lower arm moves longitudinally relative to said upper arm to perform the protrusive movement of the dental models; and said journals may independently longitudinally slide on said journal receiving surface such that said front end of said lower arm moves laterally relative to said upper arm to perform the lateral movement of the dental model; and biasing means for biasing said pair of journals toward a predetermined position on said journal receiving surfaces including:
a cantilever spring including:
a front end connected to said upper arm near said front end of said upper arm; and
a rear end.

2. The dental articulator of claim 1 wherein:
said biasing means biases said journals to the centric position.

3. The dental articulator of claim 1 wherein:
said rear end of said cantilever arm is rearward of said upper arm.

4. The dental articulator of claim 1 including:
longitudinal restraining means for restraining longitudinal travel of said journals on said journal receiving surface.

5. The dental articulator of claim 4 wherein:
said longitudinal restraining means includes a rear stop.

6. The dental articulator of claim 1 including:
lateral restraining means for restraining relative individual travel of said journals on said journal receiving surface.

7. The dental articulator of claim 6 wherein:
said lateral restraining means includes enlargements on said journals that encounter said upper arm.

8. The dental articulator of claim 1 wherein:
said upper attaching means includes:
a cooperating ball and socket.

9. The dental articulator of claim 1 wherein:
said lower attaching means includes:
a cooperating ball and socket.

10. A dental articulator for connecting upper and lower dental models, each having a front and a rear, the front to rear direction defining the longitudinal direction; said dental articulator including:
an upper arm including:
a front end including:
upper attaching means for attaching said front end of said upper arm to the upper dental model;
a rear end;
a bottom;
a top including:
a pair of laterally spaced, longitudinally oriented slots, each including:
a bottom surface for receiving a journal; and
biasing means; and
a lower arm including:
a front end including:
lower attaching means for attaching said front end of said lower arm to the lower dental model;
a top;
a bottom;
a rear end;
a pair of laterally spaced, laterally oriented journals adapted for disposition on said bottom surfaces of said slots such that: said lower arm may pivot about said journals relative to said upper arm to perform the opening and closing motion of the dental models; said journals may jointly longitudinally slide on said journal receiving surfaces such that said lower arm moves longitudinally relative to said upper arm to perform the protrusive movement of the dental models; and said journals may independently longitudinally slide on said journal receiving surface such that said front end of said lower arm moves laterally relative to said upper arm to perform the lateral movement of the dental model; wherein
said biasing means biases said pair of journals toward a predetermined position on said bottom surfaces; said biasing means including:
a cantilever spring including:
a front end connected to said upper arm near said front end of said upper arm; and
a rear end.

11. The dental articulator of claim 10 wherein:
said biasing means biases said journals to the centric position.

12. The dental articulator of claim 10 wherein:
said rear end of said cantilever arm is rearward of said upper arm.

13. The dental articulator of claim 10 including:
restraining means for restraining longitudinal travel of said journals on said journal receiving surface.

14. The dental articulator of claim 13 wherein:
said restraining means includes a rear stop.

* * * * *